US00PP35678P2

(12) United States Plant Patent
Slaughter et al.

(10) Patent No.: US PP35,678 P2
(45) Date of Patent: Mar. 12, 2024

(54) ALMOND TREE NAMED 'BURALMFOUR'

(50) Latin Name: ***Prunus amygdalus* Batsch.**
Varietal Denomination: Buralmfour

(71) Applicant: The Burchell Nursery, Inc., Oakdale, CA (US)

(72) Inventors: John K. Slaughter, Fresno, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 18/128,845

(22) Filed: Mar. 30, 2023

(51) Int. Cl.
*A01H 5/08* (2018.01)
*A01H 6/74* (2018.01)

(52) U.S. Cl.
USPC ..... Plt./155
CPC ..... *A01H 6/7427* (2018.05)

(58) Field of Classification Search
USPC ..... Plt./155
CPC ..... A01H 5/0825
See application file for complete search history.

(56) References Cited

U.S. PATENT DOCUMENTS

PP21,934 P3 5/2011 Crocker
PP28,466 P3 10/2017 Gerdts et al.
PP32,301 P2 10/2020 Slaughter

*Primary Examiner* — Kent L Bell
(74) *Attorney, Agent, or Firm* — Randall Danskin, P.S.

(57) ABSTRACT

A new and distinct variety of almond tree, which is denominated varietally as 'Buralmfour', is described with self-fertility and which produces an attractively light-colored kernel that is mature for harvesting on approximately August 19 to August 25 under the ecological conditions prevailing in the San Joaquin Valley of central California.

9 Drawing Sheets

Latin name: Genus: *Prunus*. Sub-Genus: *Amygdalus*. Species: *Prunus amygdalus* Batsch.

Variety denomination: The invention relates to a new, novel, and distinct variety of almond tree, a *Prunus amygdalus* Batsch, with a variety denomination hereinafter as 'Buralmfour'.

SUMMARY

The present variety of almond tree resulted from an on-going program of fruit and nut tree breeding. The purpose of this program was to improve the commercial quality of deciduous fruit and nut varieties and rootstocks by creating and releasing promising selections of *Prunus* species. To this end both controlled and hybrid cross pollinations were made each year in order to produce seedling populations from which improved progenies were evaluated and selected.

PRIOR VARIETIES

The seedling, 'Buralmfour,' was originated by the applicant and selected from a population of seedlings growing in its experimental orchards, which are located near Fowler, California, USA. The seedlings, grown on their own roots, were derived from a cross made in early February 2006 using the almond 'Tuono' (unpatented) tree, which was used as the seed parent, and the almond 'Monterey' (U.S. Pat. No. PP3,483) tree, which was used as the pollen parent. After a period of stratification, the seed was placed in a greenhouse by population and then field planted for tree establishment, ultimately to exhibit fruit for evaluation.

ORIGIN

One almond seedling from this population, which is the present variety, exhibited especially desirable characteristics and was then designated as 'P16.022'. This seedling was marked for subsequent observation. After the 2010 fruiting season, the new variety of almond tree was selected for advanced evaluation and repropagation.

ASEXUAL REPRODUCTION

Asexual reproduction of this new and distinct variety of almond tree was accomplished by budding the new almond tree onto 'Nemaguard' Rootstock (unpatented). This was performed by the applicant in its experimental orchards, which are located near Fowler, California, USA. Subsequent evaluations of these asexually reproduced plants have shown those asexual reproductions run true to the original tree. All characteristics of the original tree and its fruit were established and appear to be transmitted through these succeeding asexual propagations.

COMPARISONS

'Buralmfour' is a new and distinct variety of almond tree, which is considered of medium size and which has a moderately vigorous and upright growth characteristic. This new tree is also a regular and productive bearer of relatively small kernels which have a very smooth pellicle, good eating qualities, and a semi-soft shell. This new almond tree has a medium chilling requirement of 450 hours. In addition to the foregoing, the new almond also exhibits self-fertility. The 'Buralmfour' almond tree bears fruit which are typically ripe for commercial harvesting and shipment on approximately August 19 to August 25, under the ecological conditions prevailing in the San Joaquin Valley of central California. In relative comparison to the 'Monterey' almond tree, which is the closest known variety to the new variety described herein, the new variety of almond tree bears almonds approximately 7 days earlier, has kernels that average 25% smaller than 'Monterey,' and further exhibits self-fertility. Accordingly, the new variety does not need a pollinator to set nuts. By comparison, the male parent, 'Monterey', is self-sterile (not self-fertile) and requires a pollinator to set nuts.

BRIEF DESCRIPTION OF THE DRAWINGS

The accompanying drawings are color photographs of the new almond tree 'Buralmfour' during the twelfth fruiting season under the ecological conditions prevailing at the orchards of the applicant, which are located near Fowler, California, USA.

Figure 1:
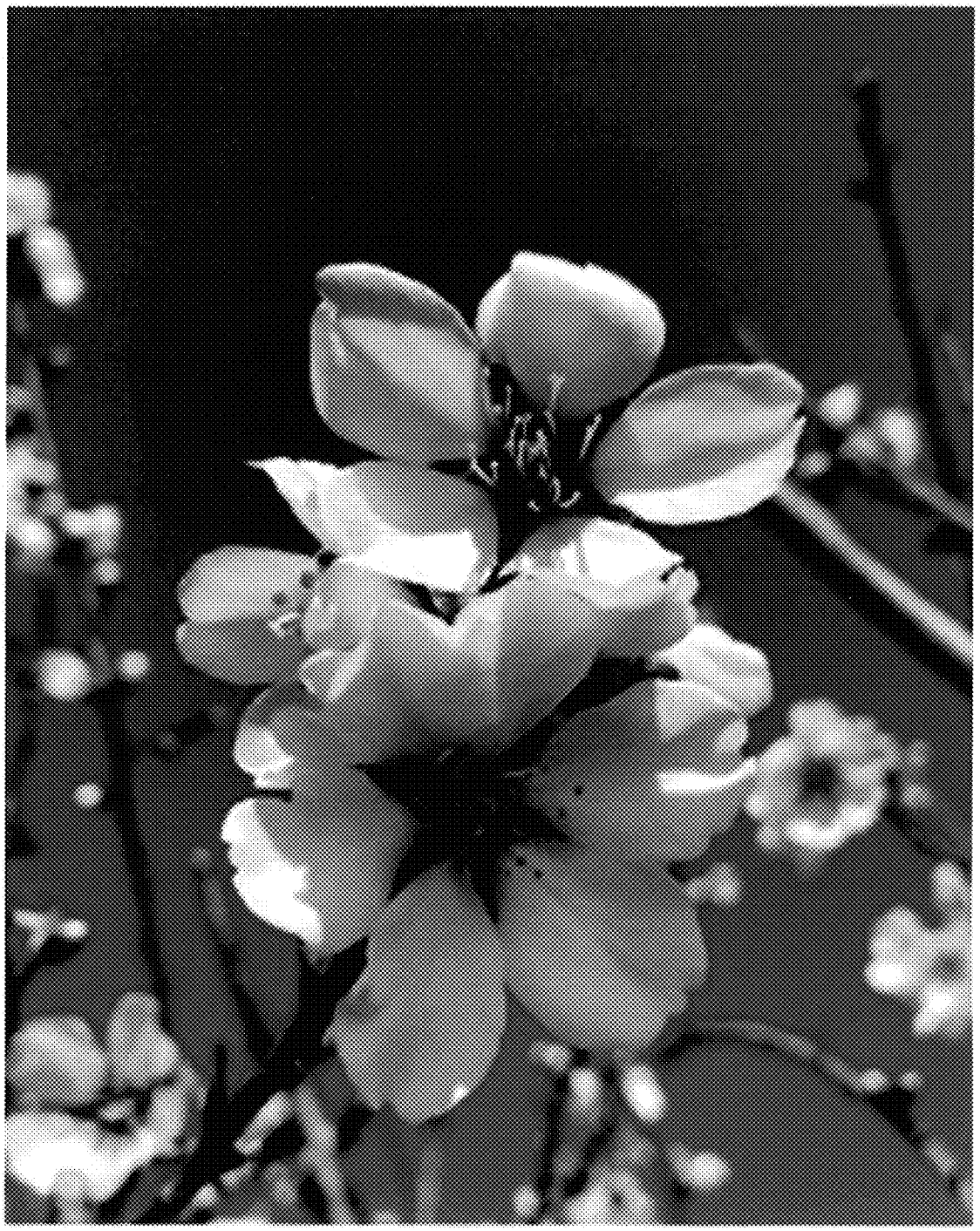
FIG. 1 focuses on two flowers in full bloom in the foreground.
Figure 2:
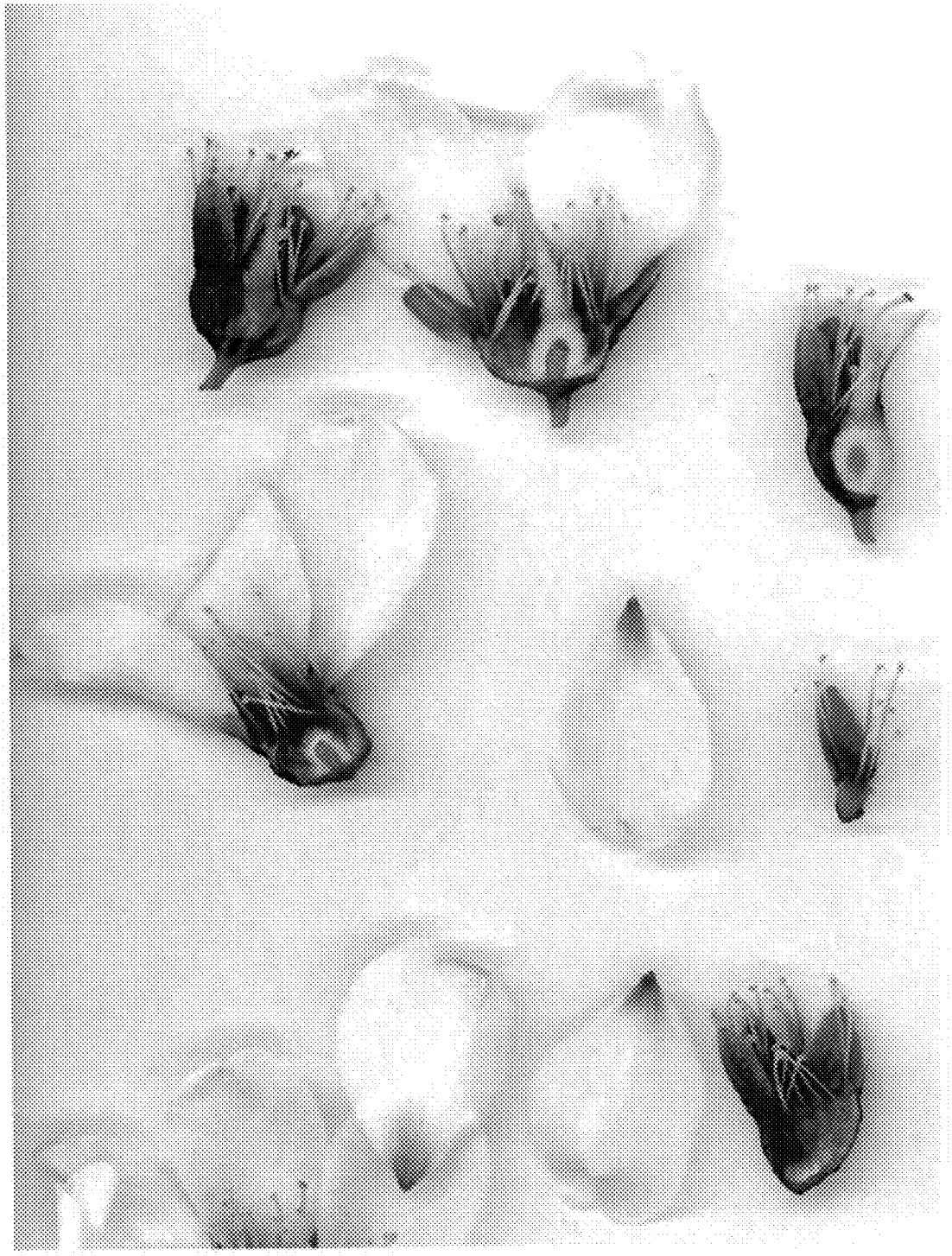
FIG. 2 shows cross sections of three flowers in the top row at various stages of bloom along with petals both attached and detached from the three flowers and the counterpart cross sections removed from the three flowers and positioned in the middle and bottom rows.
Figure 3:
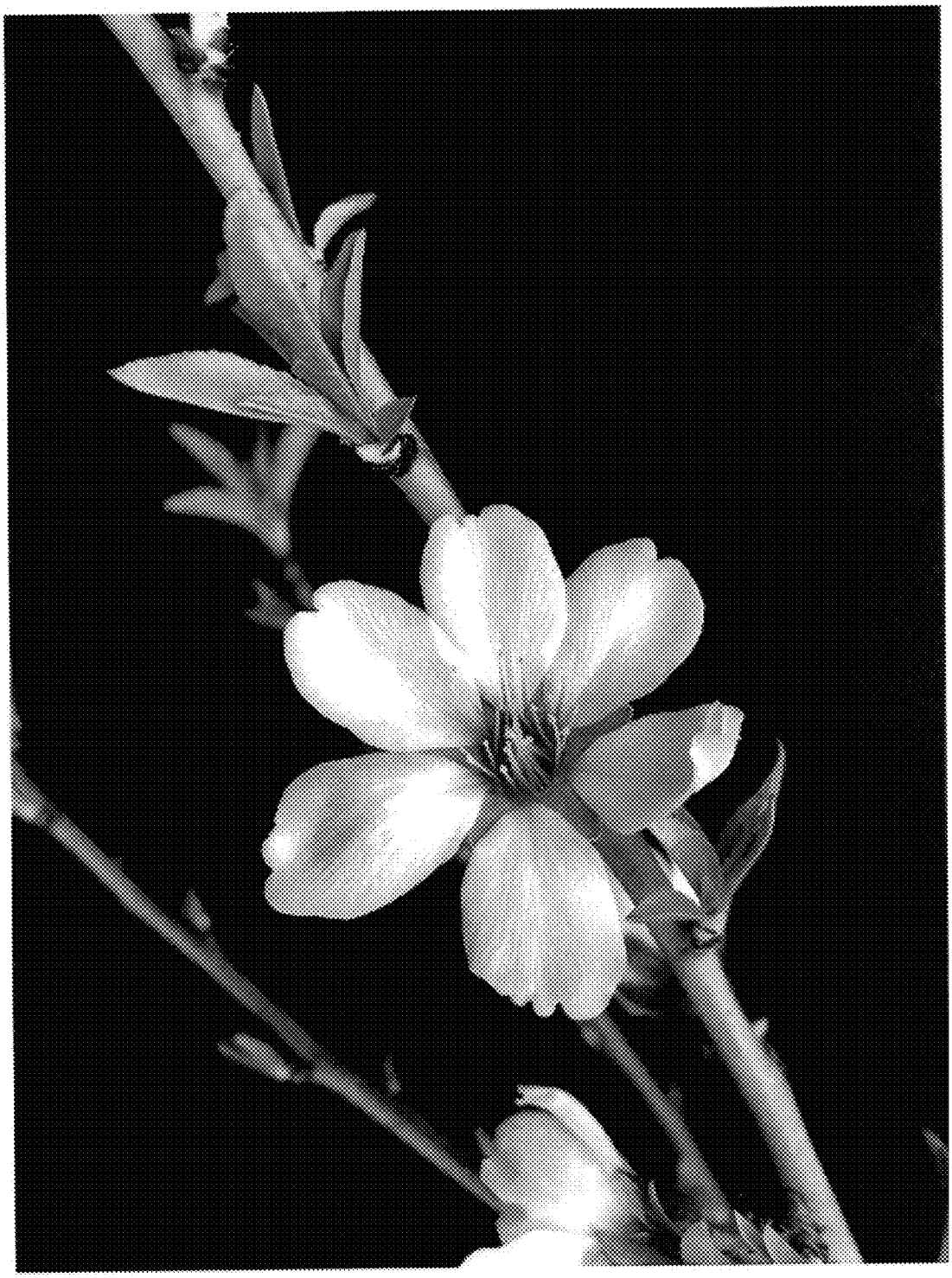
FIG. 3. focuses on one flower at full bloom and immature leaves on a portion of a branch in the foreground.
Figure 4:
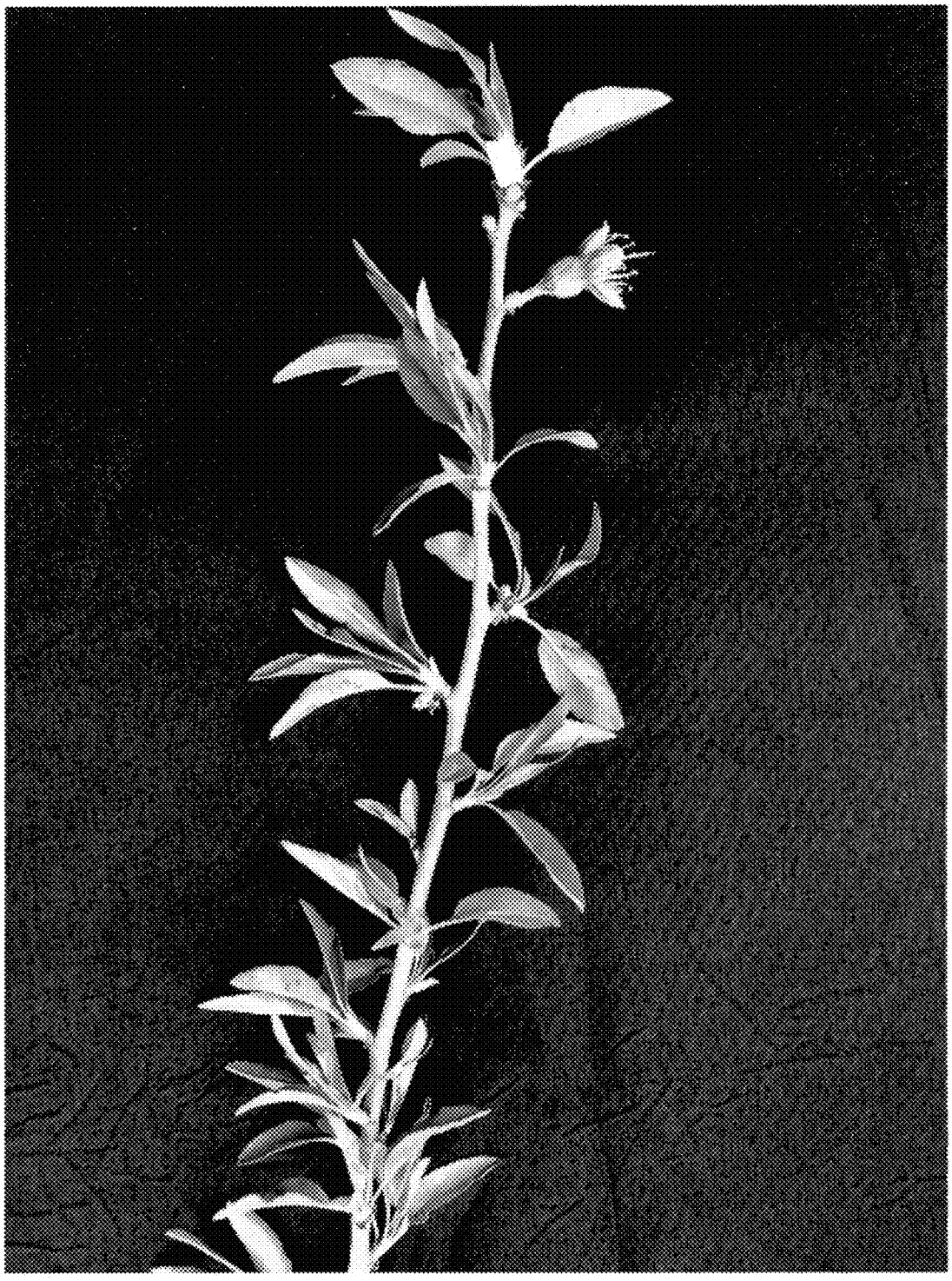
FIG. 4 shows a portion of a branch with immature leaves and one flower after petal fall.
Figure 5:
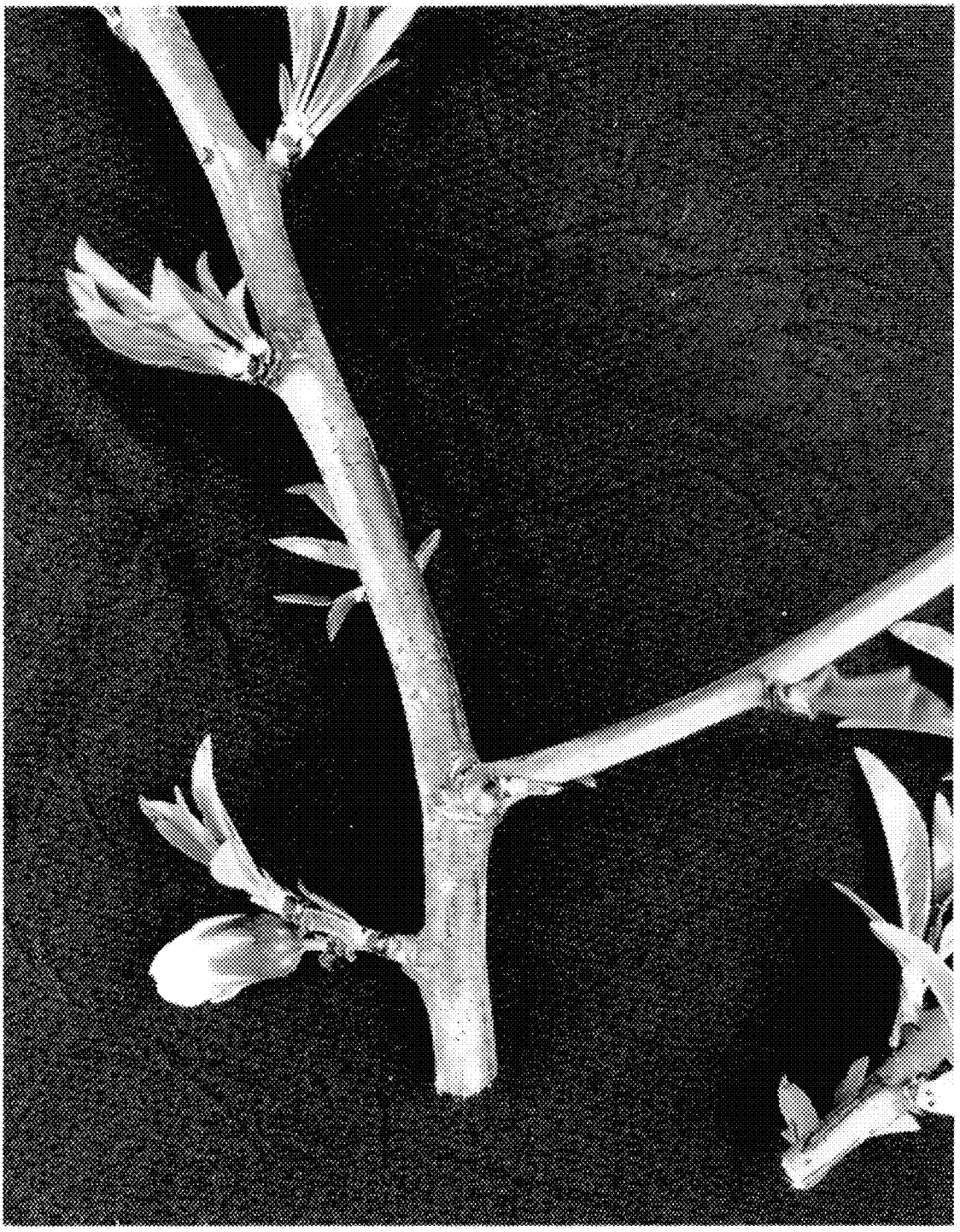
FIG. 5 shows a portion of a mature branch with immature leaves and one flower at popcorn stage.
Figure 6:
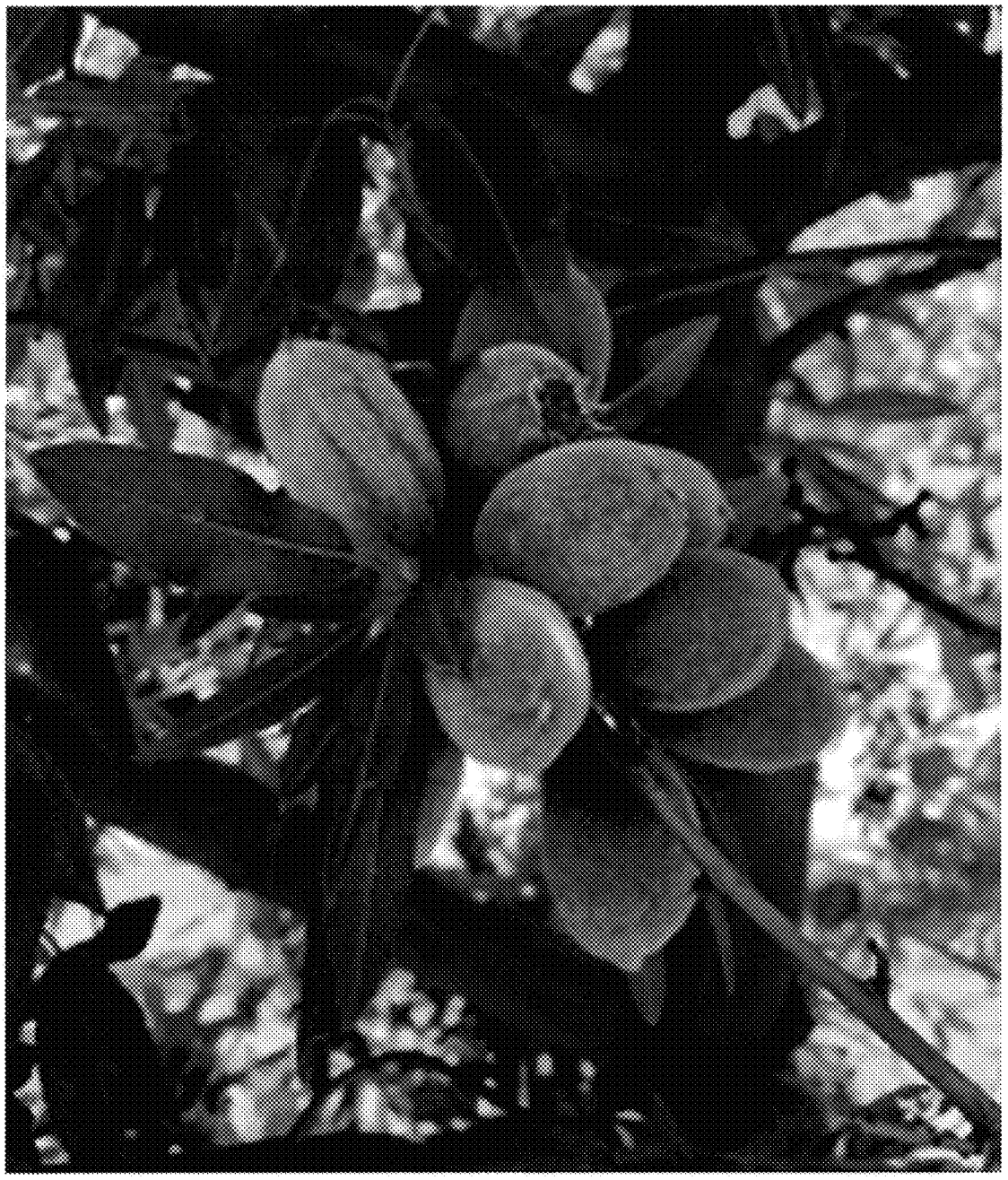
FIG. 6 shows immature almonds on a tree prior to harvest.
Figure 7:
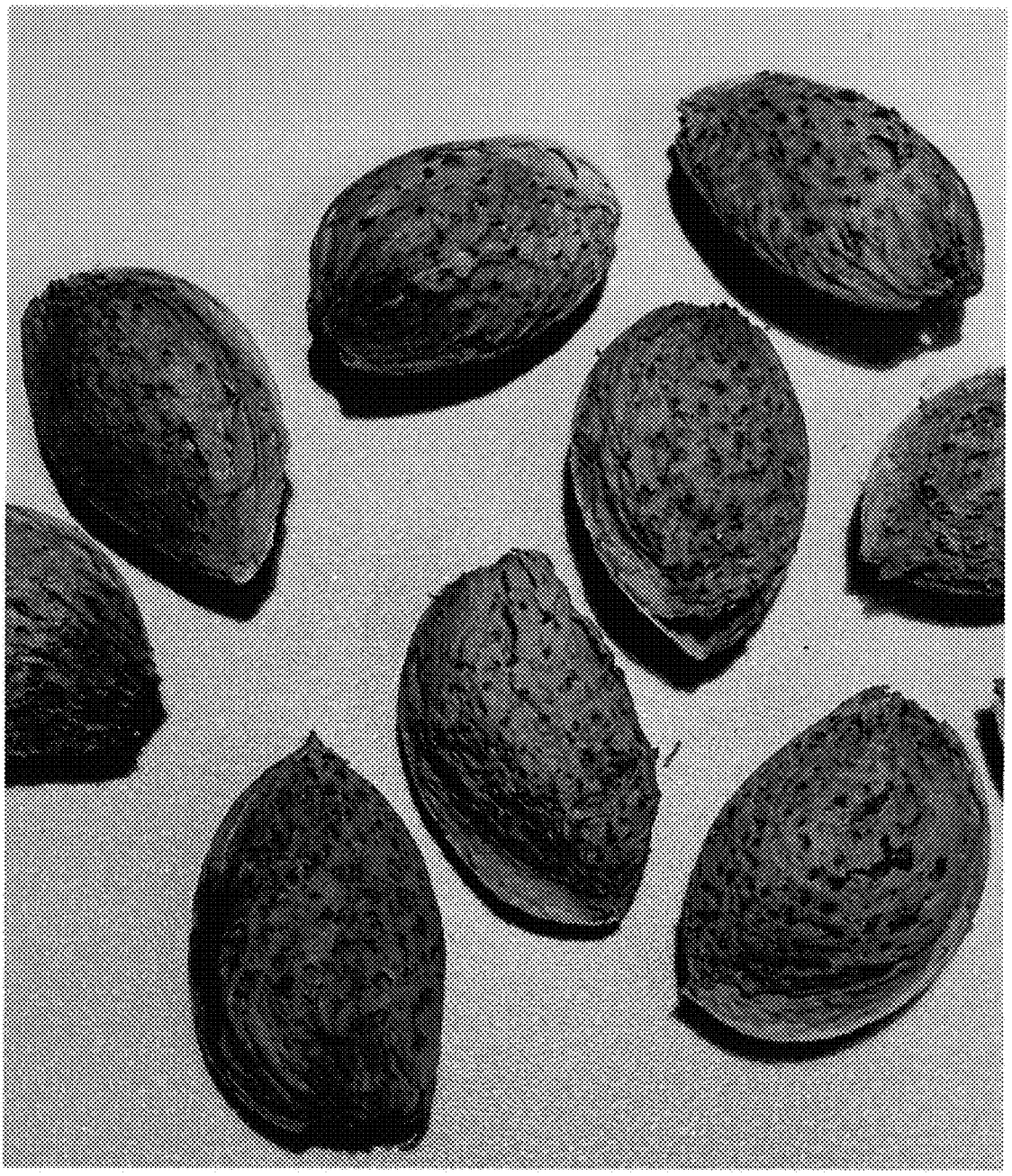
FIG. 7 shows unshelled almonds with hulls removed in a lateral view.
Figure 8:
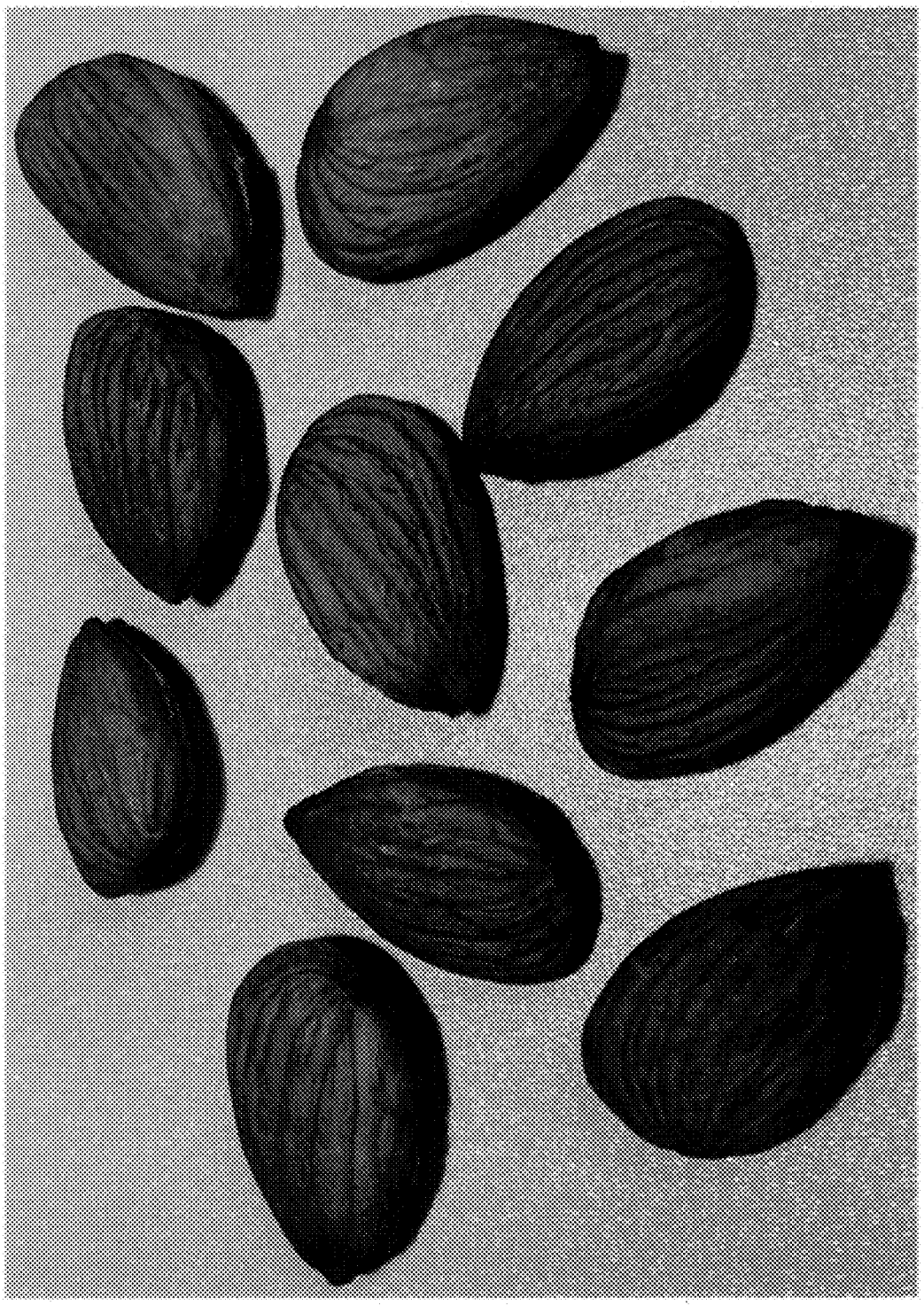
FIG. 8 shows kernels with shells removed in a lateral view, which demonstrates the kernel veining, the relative shape, and the pellicle color.
Figure 9:
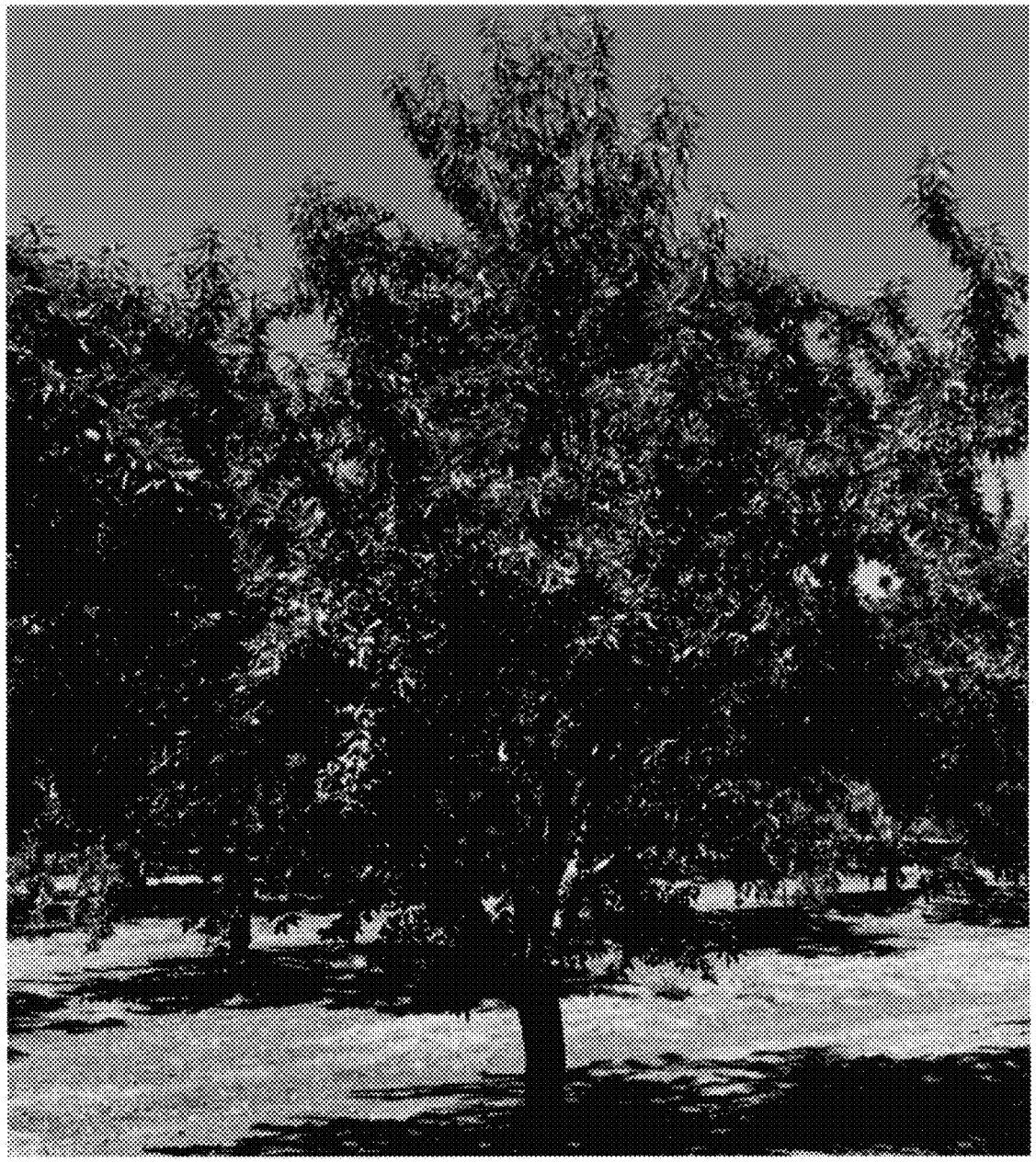
FIG. 9 shows a mature tree with its spreading growth characteristic.

The colors in these photographs are as nearly true as is reasonably possible in a color representation of this type. Due to variations in color printers and/or chemical development, processing, and printing, the colors of the plant parts depicted in these photographs may, or may not, be accurate when compared to the actual specimen. For this reason, color references are made to the color plates (Royal Horticultural Society Colour Chart, Sixth Edition (2015), hereinafter, "RHS") and descriptions provided.

DETAILED BOTANICAL DESCRIPTION

Not a Commercial Warranty. The following detailed description was prepared solely to comply with the provisions of 35 U.S.C. § 112 and does not constitute a commercial warranty (either expressed or implied) that the present variety will, in the future, display the botanical, pomological, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of tree.

Referring more specifically to the pomological details of this new and distinct variety of almond tree, the following has been observed during the tenth fruiting season under the ecological conditions prevailing at the orchards of the applicant, which are located near Fowler, California, USA. Common color names are also occasionally used.

Tree:

*Size.*—Generally considered medium and upright in its growth pattern as compared to other known commercial almond cultivars. The tree of the present variety was pruned to a height of approximately 700.0 centimeters (cm) to about 730.0 cm at commercial maturity. Tree pruning, canopy development, and ultimate stature of almond orchards are a matter of variety, rootstock, soil potential, cultural inputs and choices. Therefore tree height can be highly variable and therefore not necessarily indicative of the current variety.

*Width.*—Approximately 655.0 cm.

*Vigor.*—Considered moderately vigorous. The present almond tree variety grew from about 200.0 cm to about 210.0 cm in height during the first growing season. The new variety was pruned to a height of approximately 150.0 cm during the first dormant season and primary scaffolds were then selected for the desired tree structure. Tree vigor can be influenced by a number of variables including soil quality, irrigation practices, nutrition, pruning, and nutrition.

*Productivity.*—Productive. Observation from the first three years of harvest indicate an increasing production range from 1,000 to 1,100 pounds of kernels per acre. When the new variety is grown in a suitable horticultural zone and under appropriate commercial conditions the current variety can produce volumes of commercial almonds. The number of the fruit set varies with the prevailing climatic conditions and the cultural practices employed and can be increased with inclusion of active beehives and proximity to compatible foreign pollen sources. Although the variety exhibits self-fertility and is capable of significant yields when planted alone it is scientifically proven that yields increase when the aforementioned practices are observed.

*Fruit bearing.*—Regular. Nut set has been more than adequate during the previous years of observation during the past 12 years on both the original seedling and on subsequent asexually reproduced trees.

*Tree form.*—Upright and typically pruned into a vase shape.

*Density.*—Considered moderately dense. It has been determined that pruning the branches from the center of the tree to obtain a resulting vase shape allows for enhanced air movement and appropriate amounts of sunlight to improve fruit wood development.

*Hardiness.*—The present tree was grown and evaluated in USDA Hardiness Zone 9. The calculated winter chilling requirements of the new tree was approximately 450 hours at a temperature below 7.0 degrees Celsius. The present variety appears to be hardy under typical central San Joaquin Valley climatic conditions.

Trunk:

*Diameter.*—Approximately 28.5 cm in diameter when measured at a distance of approximately 15.24 cm above the soil level. This measurement was taken at the end of the twelfth growing season.

*Bark texture.*—Considered moderately rough, with numerous folds of papery scarfskin being present. Since bark development and coloration change with advancing tree age, this characteristic varies with the tree vigor, age, and regional conditions.

*Lenticels.*—Numerous flat, oval lenticels are present. The lenticels range in size from approximately 4.0 millimeters (mm) to about 6.0 mm in width and between about 1.0 and about 2.0 mm in height. The development and size of the trunk lenticels can be influenced, to some degree, by the ambient growing conditions. As trees of this variety mature, lenticels are present, but they are generally covered by increasing layers of cork (mature bark) and therefore become less apparent.

*Lenticel color.*—Considered an orange brown (RHS Greyed-Orange Group 163C).

*Bark coloration.*—Variable, but it is generally considered to be a greyed brown (RHS Greyed-Orange Group 166A). This bark description was taken from trees in their twelfth leaf which have ruptured the scarf skin with deep furrowing as the trunk expands with age. It should be noted that the coloration of the bark can be influenced by exposure to sunlight and humidity.

Branches:

*Size.*—Considered medium for the variety.

*Diameter.*—Average as compared to other almond varieties. The branches have a diameter of about 22.0 cm when measured during the twelfth year after grafting.

*Surface texture.*—Average; furrowing of bark usually occurs by the fourth year of development.

*Crotch angles.*—Primary branches are considered variable and are usually growing at an angle of about 42 to about 56 degrees when measured from a horizontal plane. This characteristic can be influenced, to some degree, by tree vigor, rootstock, time and severity of pruning, and other cultural conditions.

*Current season shoots surface texture.*—Substantially glabrous.

*Current season shoots internode length.*—Approximately 15.0 mm to 35.0 mm between nodes. Greater internodal intervals exist nearer the basal end of the shoot and shorter internodal intervals are exhibited nearer the apical shoot tip.

*Current season shoots color.*—Medium-light green (RHS Yellow-Green Group 144C). The color of new shoot tips is considered a bright and shiny green (RHS Yellow-Green Group 145B). The vegetative shoot color can be significantly influenced by plant nutrition, irrigation practices, and exposure to sunlight.

*Color of mature branches.*—Approximately grey brown (RHS Greyed-Orange Group 166C).

Leaves:

*Size.*—Considered medium-large for the species. Leaf measurements have been taken from vigorous, upright, current-season growth at approximately mid-shoot. It should be understood that the leaf size is often influenced by prevailing growing conditions, quality of sunlight, and the location of the leaf within the tree canopy. For this reason, leaf sizes can vary significantly based upon the amount of ambient light and other cultural factors listed above.

*Leaf length.*—Approximately 155.0 to about 178.0 mm.

*Leaf width.*—Approximately 33.0 to about 36.0 mm.

*Leaf base-shape.*—The leaves generally exhibit equal marginal symmetry relative to the leaf longitudinal axis.

*Leaf form.*—Lanceolate.

*Leaf tip form.*—Acuminate.

*Leaf color, upper leaf surface.*—Dark green (approximately RHS Yellow-Green Group 137A).

*Leaf texture.*—Upper leaf surface somewhat smooth and regular. Lower leaf texture glabrous with slight pubescence.

*Leaf color, lower leaf surface.*—Light to medium green (approximately RHS Yellow-Green Group 137C).

*Leaf venation.*—Pinnately veined.

*Mid-vein color.*—Considered a light, yellow-green (approximately RHS Yellow Green Group 150C) in the early to mid-period of the growing season.

*Leaf margins.*—Considered entire and smoothly crenate; occasionally doubly crenate. Form — Considered smooth. Uniformity — Considered generally uniform.

*Leaf petioles.*—Form. — Considered canaliculated and having a more pronounced trough when viewed from the dorsal aspect. The petiole margin is considered rounded when viewed from the ventral aspect. Size — Considered medium-large for the species. Length — About 14.0 to about 33.5 mm. Diameter — About 1.5 to about 2.0 mm. Color — Light yellow green (approximately RHS Yellow-Green Group 149C).

*Leaf glands.*—Size — Considered very small for the species; approximately 0.5 cm in length and about 0.5 cm in height. Number — Generally one and less common two glands appear per marginal side are found. Occasionally glands are only present on one side. More rarely no classifiable glands are present. Type — Glands located at the base of the leaf are predominantly globose in shape.

*Color.*—Considered a medium, light brown, approximately (RHS Yellow-Green Group N144B).

*Leaf stipules.*—Size — Small for this species. Length — 1.0-2.0 mm. Width — 0.3- 0.5 mm. Number — Typically, 2 per leaf bud and up to 6 per shoot tip. Form — Lanceolate in form and having a serrated marginal edge. Color — Green (approximately RHS Green Group 139B) when young, but graduating to a brown color (approximately RHS Greyed-Orange Group 165A) with advancing senescence. The leaf stipules are generally considered to be early deciduous.

Flower buds:

*Hardiness.*—No winter injury (bud death) has been noted during the years of observation in the central San Joaquin Valley. The new variety of almond tree has not been intentionally subjected to drought, cold, or heat stress and therefore this information is not available.

*Size.*—Variable and dependent on the state of maturity. The flower buds as described were observed approximately 7 days prior to bloom.

*Length.*—Approximately 15.0 mm.

*Diameter and shape.*—Approximately 10.0 mm; oblong to ovatus shape.

*Surface texture.*—Pubescent.

*Orientation.*—Considered appressed, but appear less so as the blossoms near opening.

*Bud scale color.*—Approximately RHS Greyed-Purple Group 185C.

Flowers:

*Date of first bloom.*—Observed on February 23, 2021.

*Blooming time.*—Considered average in relative comparison to other commercial almond cultivars grown in the central San Joaquin Valley. The date of full bloom was observed on Mar. 1, 2021. Approximately 13-14 days after the 'Nonpareil' (unpatented) variety. The date of full bloom varies slightly with climatic conditions and prevailing cultural practices.

*Duration of bloom.*—Approximately 8 days. Occasionally 10 days or slightly more. This particular characteristic varies slightly with the prevailing climatic conditions.

*Flower class.*—Considered a perfect flower; complete and perigynous.

*Flower type.*—The variety is considered to have a showy type flower. Petals are largely unappressed relative to the vertical axis of the flower.

*Flower size.*—Considered medium-large for the species. The flower diameter at full bloom is approximately 40.0 to 45.0 mm.

*Bloom density.*—Considered abundant, typically 30% more flowers per tree compared to 'Monterey.'

*Flower bud frequency.*—Generally three to four flower buds appear per node; occasionally two flower buds per node is observed. Larger numbers of flower buds are present on mature complex spurs.

*Petal.*—Size — Generally considered medium for the species. Length — Approximately 20.0 to 22.0 mm. Width — Approximately 14.0 to 16.0 mm. Form — Considered broadly ovate. Count — Nearly always 5. Texture — Both the upper and lower surfaces of the petal are soft and smooth to the touch with a fine, velvety texture. Color — Considered a pinkish white at the popcorn stage (RHS White Group N155B) and becomes lighter during enfloration to nearly a pure white (RHS White Group N155D).

*Fragrance.*—Slightly floral and sweet; similar to warm honey.

*Petal claw.*—Generally — Small, short coming to a point the end of which is purplish-red (RHS Red-Purple Group N57B). Form — The claw is considered obovate and is generally small and more pointed. Length — Approximately 3.0-4.0 mm. Width — Approximately 1.0 to 2.0 mm.

*Petal margins.*—Generally considered variable, from nearly smooth to moderately undulate.

*Petal apex: Generally.*—Often the petal margin exhibits a deep and narrow recess at the tip. Length — Approximately 4.0 mm. Depth — Approximately 2.0 mm.

*Flower pedicel.*—Length — Considered medium-long with an approximate length of about 4.5 to about 5.0 mm. Diameter — Approximately 1.5 mm. Color — A moderate yellowish green (approximately RHS Green Group 138A), depending on pedicel and timing of visual observance. Surface — Smooth.

*Floral nectaries color.*—Considered a strong orange (approximately RHS Orange Group 26B).

*Calyx.*—Surface texture — Smooth to slightly glabrous with small (0.025 mm) infrequent hairs. Color — A dull greyish purple (approximately RHS Greyed-Purple Group 184A).

*Sepals.*—Surface texture — The surface has a short, fine pubescent texture. Number — 5 sepals. Size — Long. Length — Approximately 11.0 to 12.0 mm. Width — Approximately 3.5 to 4.0 mm. Shape — Generally ovatus. Margin — Considered smooth and entire. Color — A strong yellow green (approximately RHS Yellow-Green Group 145A).

*Anthers.*—Generally — Average in size. Approximately 10 to 12 mm. Color — A strong orange yellow when viewed dorsally at dehiscence (approximately RHS Orange Group 24B). Number — Typical number of observed anthers per flower is approximately 27, which are at the same level to slightly below the stigma.

*Pollen production.*—Pollen is abundant and has a yellow color (approximately RHS Yellow Group 13C).

*Fertility.*—Self-fertile.

*Filaments.*—Size — Approximately 7.0 to 10.0 mm in length. Approximately 0.5 to 0.75 mm in width. Color — Considered deep purplish pink (RHS Red-Purple Group N57D) transitioning to a strong white (RHS White Group NN155C) moving up the filament towards the anthers.

*Pistil.*—Number — Nearly always one. Generally — Medium in length. Length — Approximately 14.0 to about 15.0 mm in length including the ovary. Color — Considered a light greenish grey (approximately RHS Greyed-Green Group 188C). Surface texture — The variety has a pubescent pistil.

Kernel:

*Maturity when described.*—Firm, dry pellicle condition. Approximately Aug. 22, 2021. The date of harvest can vary with the prevailing climatic conditions, crop loads, and cultural practices.

*Size.*—Considered small to medium and very uniform. It generally compares to the 'Ruby' variety (U.S. Pat. No. PP1,698) in size.

*Average kernel length.*—24.65 mm. Size range is approximately 23.57 to about 26.17 mm.

*Average kernel width.*—14.84 mm. Size range is approximately 12.0 to about 15.0 mm.

*Average kernel thickness.*—7.9 mm. Size range is approximately 7.0 to about 8.0 mm. These dimensional characteristics are quite dependent upon crop load and the prevailing cultural practices.

*Kernel form.*—Generally the kernels are very uniform in shape and relatively round and wide at the middle. The base is flat and wide then becomes thick and plump in the middle rounding to a more pointed apex at the tip. Compared to 'Ruby' variety the kernels of the present variety are slightly broader and slightly lighter.

*Color.*—Considered a light golden brown (RHS Greyed-Orange 164C).

*Apex shape.*—Rounded to slightly retuse.

*Base shape.*—Slightly oblique relative to the verticle axis.

*Pellicle thickness.*—Considered medium in thickness and tenacious to the flesh.

*Surface texture.*—Smooth with little to no pubescence. Surface veining is present throughout the pellicle.

*Color of veins.*—Considered a medium brown approximately (RHS Greyed-Orange 166D).

*Taste.*—Mild, pleasant, slightly sweet.

*Kernel weight.*—Approximately 1.38 grams/kernel although the weights of kernels can be highly affected by climatic conditions and cultural practices. It is possible to observe kernels with the same size, but higher and lower weight.

*Texture.*—Firm and dense.

*Aroma.*—Not apparent.

*Eating quality.*—Considered very good.

*Stem scar/hilum.*—Measured 5.9 mm in height and 4.2 mm in width on the kernel.

Shell:

*Type.*—Considered a freestone.

*Size.*—It is generally considered to be small to medium for the species. The shell size varies significantly depending upon the tree vigor, the crop load, and the prevailing growing and cultural conditions under which the tree was grown.

*Length.*—34.35 mm. Average size range is approximately 32.0 to about 35.0 mm.

*Width.*—21.88 mm. Average size range is approximately 21.0 to about 23.0 mm.

*Thickness.*—13.45 mm. Average size range is approximately 12.0 to about 14.0 mm.

*Form.*—Roughly ovoid.

*Shell base shape.*—Considered shortly attenuate.

*Apex shape.*—The shell exhibits a slight to prominently cuspinate apex.

*Shell surface texture.*—Considered reasonably rough with considerable pitting with almost non-existent furrowing or ridging and a bit of flakiness as the shell dries and some of the outer portions of the shell sluff off.

*Ventral edge.*—The ventral edge generally exhibits a thin, narrow, and fine protruding fin at the sutural margin approximately 2-3 mm wide.

*Dorsal edge shape.*—Generally considered even. The folds of the surface ridges appearing on the external margins often end gently along the suture and completely closes around the kernel sealing it inside.

*Shell color.*—The color of a mature, dry stone is generally considered a dull brown (approximately RHS Greyed-Orange Group 164C).

*Hull.*—Shape — Elliptical. Length — 37mm average. Width — 28 mm average. Thickness — 3.25 mm average. Texture — Smooth and velvety with short fine hairs becoming more wrinkled as the hulls split closer to harvest. Weight — Average weight of the hull alone prior to harvest with the shell and nut removed is 2.5 grams. Adherence — The hull pulls away from the shell starting at the suture as it dries causing the nut to come free at harvest with relative ease compared to the commercial variety Monterey. The hull is further removed with ease in the hulling process. Suture — Tight and closed during the Summer then splitting open about 1 mm from the tip down approximately one week before harvest. Color — Mid-Summer color Yellowish Green (RHS Pale Yellow Green Group 194D). As the hulls dry, they become more of a Yellowish Grey (RHS Yellowish Grey Group 156C).

*Use.*—The present variety 'Buralmfour' is considered to be an almond tree of the mid-season to late maturity, which produces kernels that are useful in various almond categories and are blanchable.

*Keeping quality.*—Appears excellent, maintaining flavor for more than a year after harvest when kept in a sealed container in a cool, dry, dark environment.

*Shipping quality.*—Similar to other commercial almond varieties; considered very good.

*Resistance to insects and disease.*—No particular susceptibilities were noted. The present variety has not been intentionally tested to expose or detect any susceptibilities or resistances to any known plant or fruit disease, insect, frost, winter injury, or other environmental factor. However, because of the closed shell suture around the kernel there is a very low incidence of worm damage to the kernel.

Although the new variety of almond tree possesses the described characteristics when grown under the ecological conditions prevailing near Fowler, California, USA, in the central part of the San Joaquin Valley of California, it should be understood that variations are to be expected in the usual magnitude and characteristics incident to changes in growing conditions, fertilization, nutrition, pruning, pest control, frost, climatic variables, and changes in horticultural management.

Having thus described and illustrated a new variety of almond tree, what is claimed to secure a plant Letters Patent is:

1. A new and distinct variety of almond tree named 'Buralmfour', substantially as illustrated and described, which is characterized principally as to novelty by self-fertility and producing an attractively light-colored kernel that is mature for harvesting on approximately August 19 to August 25 under the ecological conditions prevailing in the San Joaquin Valley of central California.

* * * * *